United States Patent [19]

Plummer

[11] Patent Number: 4,609,732
[45] Date of Patent: Sep. 2, 1986

[54] 2-(ALPHA-PERHALOALKYLBENZYLOXY)-PYRIDYL INSECTICIDE INTERMEDIATES

[75] Inventor: Ernest L. Plummer, Yardley, Pa.

[73] Assignee: FMC Corporation, Philadelphia, Pa.

[21] Appl. No.: 816,175

[22] Filed: Jan. 3, 1986

[51] Int. Cl.$^4$ .......................................... C07D 405/12
[52] U.S. Cl. .................... 546/269; 546/270; 546/297
[58] Field of Search .................. 546/297, 270, 269

[56] References Cited

U.S. PATENT DOCUMENTS

| 4,013,717 | 3/1977 | Wellinga et al. | 260/553 |
|---|---|---|---|
| 4,173,639 | 11/1979 | Suhr | 260/553 |
| 4,264,605 | 4/1981 | Suhr et al. | 424/263 |
| 4,350,706 | 9/1982 | Brouwer et al. | 424/322 |

OTHER PUBLICATIONS

Kobus Wellinga et al., *J. Agr. Food Chem.*, 21, 348 and 993 (1973).
Mukaiyama et al., *Chem. Lett.*, 1177–1180, 80, (1976).

*Primary Examiner*—Henry R. Jiles
*Assistant Examiner*—J. Richter
*Attorney, Agent, or Firm*—R. L. Hansen; H. R. Ertelt

[57] ABSTRACT 2-(Alpha-perhaloalkylbenzyloxy)pyridyl compounds of the following structural formula are intermediates to N-[(alpha-perhaloalkylbenzyloxy)pyridyl]-N'-benzoylurea insecticides:

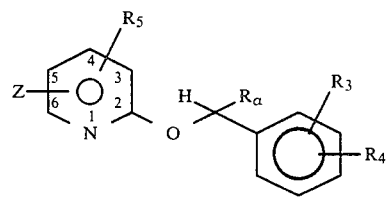

in which $R_\alpha$ is a perhaloalkyl substituent;

$R_3$ is selected from the group consisting of -hydrogen, -halogen and -phenylthio;

$R_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino; or $R_3$ and $R_4$ at adjacent ring positions constitute a —OCH$_2$O—, —CH$_2$C(CH$_3$)$_2$O—, or —CF$_2$CF$_2$O— bridge;

$R_5$ is -hydrogen or -lower alkyl; and

Z is -amino or -nitro.

11 Claims, No Drawings

2-(ALPHA-PERHALOALKYLBENZYLOXY)PYRIDYL INSECTICIDE INTERMEDIATES

This invention pertains to organic chemical compounds; specifically, certain 2-(alpha-perhaloalkylbenzyloxy)pyridyl compounds which are intermediates useful in the preparation of insecticides.

The U.S. patent application of Ernest L. Plummer, Ser. No. 801,365, filed Nov. 25, 1985, discloses novel N-[(alpha-perhaloalkylbenzyloxy)pyridyl]-N'-benzoylurea insecticides, as well as a general process for preparing them. The referenced application is incorporated herein by reference.

Key intermediates in the preparation of the aforesaid insecticides are 2-(alpha-perhaloalkylbenzyloxy)pyridyl compounds of the following structural formula. These intermediates are the subject of this invention.

wherein
$R_a$ is a perhaloalkyl substituent;
$R_3$ is selected from the group consisting of -hydrogen, -halogen and -phenylthio;
$R_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino; or
$R_3$ and $R_4$ at adjacent ring positions constitute a $-OCH_2O-$, $-CH_2C(CH_3)_2O-$, or $-CF_2CF_2O-$ bridge;
$R_5$ is -hydrogen or -lower alkyl; and
Z is -amino or -nitro.

The terms "halo" and "halogen" when employed herein mean fluorine, chlorine or bromine. The term "lower" modifying "alkyl," "alkoxy," and the like implies a straight or branched hydrocarbon chain of 1-6, preferably 1-4, carbon atoms; "halo" coupled with another term means one or more hydrogen atoms has been replaced by halogen; "perhalo" coupled with another term means all the hydrogen atoms have been replaced by halogen.

Among the aforesaid compounds, the most attractive insecticides result from those intermediates in which $R_5$ is at the 3-position. Additionally, the preferred compounds have the $R_3$ and $R_4$ substituents in the 3- and 4-positions, respectively. Specific compounds of interest include 2-(2,2,2-trifluoroethoxy-1-phenyl)-3-methyl-5-nitropyridine, 5-amino-2-(2,2,2-trifluoromethoxy-1-phenyl)-3-methylpyridine, 2-[1-(2,2,3,3-tetrafluoro-2,3-dihydrobenzofuran-5-yl)-2,2,2-trifluoroethoxy]-5-nitropyridine, 5-amino-2-[1-(2,2,3,3-tetrafluoro-2,3-dihydrobenzofuran-5-yl)-2,2,2-trifluoroethoxy]pyridine, 2-[1-(1,3-benzodiox-5-yl)-2,2,2-trifluoroethoxy]-5-nitropyridine, 5-amino-2-[1-(1,3-benzodiox-5-yl)-2,2,2-trifluoroethoxy]pyridine, 2-[1-(1,3-benzodiox-5-yl)-2,2,3,3,4,4,4-heptafluorobutoxy]-3-methyl-5-nitropyridine, 5-amino-2-[1-(1,3-benzodiox-5-yl)-2,2,3,3,4,4,4-heptafluorobutoxy]-3-methylpyridine, 2-[2,2,3,3,3-pentafluoro-1-(2,3-dihydro-2,2-dimethylbenzofuran-5-yl)propoxy]-3-methyl-5-nitropyridine, and 5-amino-2-[2,2,3,3,3-pentafluoro-1-(2,3-dihydro-2,2-dimethylbenzofuran-5-yl)propoxy]-3-methylpyridine.

The compounds of this invention in which Z is -nitro are prepared by condensing an appropriately substituted 2-chloro-nitropyridine with an appropriately substituted perhaloalkyl alcohol. The corresponding compounds in which Z is -amino are prepared by reducing the -nitro derivatives. Preparation of the compounds of this invention will be clarified by reference to the following Examples.

EXAMPLE 8a

2-[1-(3,4-Dichlorophenyl)-2,2,2-trifluoroethoxy]-5-nitropyridine

Under a dry argon atmosphere a solution of 2-chloro-5-nitropyridine (1.6 g, 0.010 mole) and 1-(3,4-dichlorophenyl)-2,2,2-trifluoroethanol (2.5 g, 0.010 mole) in dimethyl sulfoxide (50 ml) was stirred for five minutes. Potassium carbonate (1.6 g, 0.011 mole) was added to the mixture in one portion. The resultant mixture was stirred at room temperature for approximately 18 hours. The mixture was transferred to a separatory funnel to which was added 50 g of ice and 75 ml of a 2N aqueous sodium hydroxide solution. This aqueous mixture was extracted with two 200 ml portions of diethyl ether. The combined extracts were dried over anhydrous magnesium sulfate and filtered. The solvent was evaporated from the filtrate under reduced pressure, leaving an oil. Purification of this oil by column chromatography on silica gel yielded 3.3 g of 2-[1-(3,4-dichlorophenyl)-2,2,2-trifluoroethoxy]-5-nitropyridine.

Analysis:
Calc'd for $C_{13}H_7Cl_2F_3N_2O_3$: C 42.53; H 1.92;
Found: C 43.38; H 1.95.

EXAMPLE 8b

5-Amino-2-[1-(3,4-dichlorophenyl)-2,2,2-trifluoroethoxy]pyridine

Hydrogenation of 2-[1-(3,4-dichlorophenyl)-2,2,2-trifluoroethoxy]-5-nitropyridine (2.7 g, 0.0074 mole) with platinum oxide (0.3 g, 0.0013 mole) in methanol (50 ml) yielded 2.5 g of 5-amino-2-[1-(3,4-dichlorophenyl)-2,2,2-trifluoroethoxy]pyridine.

Additional 2-(alpha-perhaloalkylbenzyloxy)pyridyl compounds within the scope of this invention are described in Table 1.

TABLE 1
2-[(Alpha-perhaloalkylbenzyloxy)pyridyl] Compounds

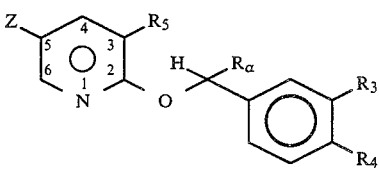

| Example | $R_5$ | $R_\alpha$ | $R_3$ | $R_4$ | NMR[a] |
|---|---|---|---|---|---|
| 1 | $CH_3$ | $CF_3$ | H | H | |
| 2 | H | $CF_3$ | H | H | |
| 3 | H | $C_2F_5$ | H | H | |
| 4 | H | $C_3F_7$ | H | H | |
| 6 | H | $CF_3$ | $SC_6H_5$ | H | |
| 8 | H | $CF_3$ | Cl | Cl | 6.6–6.9 (Z = $NO_2$) |
| 9 | H | $C_2F_5$ | Cl | Cl | |
| 10 | H | $C_3F_7$ | Cl | Cl | |
| 11 | H | $CF_3$ | —OCH$_2$O— | | 6.5–6.8 (Z = $NO_2$), 6.3–6.6 (Z = $NH_2$) |
| 12 | H | $C_2F_5$ | —OCH$_2$O— | | |
| 13 | H | $C_3F_7$ | —OCH$_2$O— | | |
| 14 | H | $C_2F_5$ | —CH$_2$C(CH$_3$)$_2$O— | | |
| 15 | H | $C_3F_7$ | —CH$_2$C(CH$_3$)$_2$O— | | |
| 16 | $CH_3$ | $C_2F_5$ | H | H | |
| 17 | $CH_3$ | $C_3F_7$ | H | H | |
| 18 | $CH_3$ | $CF_3$ | H | Cl | 6.6–6.9 (Z = $NO_2$) |
| 19 | $CH_3$ | $CF_3$ | Cl | Cl | |
| 20 | $CH_3$ | $C_2F_5$ | Cl | Cl | |
| 21 | $CH_3$ | $C_3F_7$ | Cl | Cl | |
| 22 | $CH_3$ | $CF_3$ | —OCH$_2$O— | | 6.3–6.6 (Z = $NH_2$) |
| 23 | $CH_3$ | $C_2F_5$ | —OCH$_2$O— | | |
| 24 | $CH_3$ | $C_3F_7$ | —OCH$_2$O— | | |
| 25 | $CH_3$ | $C_2F_5$ | —CH$_2$C(CH$_3$)$_2$O— | | |
| 26 | $CH_3$ | $C_3F_7$ | —CH$_2$C(CH$_3$)$_2$O— | | |
| 27 | $CH_3$ | $C_3F_7$ | Cl | N(CH$_2$CH=CH$_2$)$_2$ | |
| 28 | H | $CF_3$ | —CH$_2$C(CH$_3$)$_2$O— | | |
| 29 | H | $CF_3$ | —CF$_2$CF$_2$O— | | 6.6–6.9 (Z = $NO_2$) |
| 30 | $CH_3$ | $CF_3$ | —CF$_2$CF$_2$O— | | 6.4–6.7 (Z = $NH_2$) |
| 31 | H | $CClF_2$ | H | H | |
| 32 | $CH_3$ | $CClF_2$ | H | H | |
| 33 | $CH_3$ | $CClF_2$ | F | $CH_3$ | |
| 34 | H | $CF_3$ | H | $SC_6H_5$ | |
| 35 | $CH_3$ | $CF_3$ | H | $OC_2H_5$ | 6.5–6.8 (Z = $NH_2$) |
| 36 | $CH_3$ | $CF_3$ | H | $CH_2OCH_3$ | |
| 37 | $CH_3$ | $CF_3$ | H | $SCH_3$ | 6.5–6.8 (Z = $NO_2$), 6.4–6.7 (Z = $NH_2$) |
| 38 | $CH_3$ | $CF_3$ | H | $SO_2CH_3$ | 6.6–6.9 (Z = $NO_2$) |
| 39 | $CH_3$ | $CF_3$ | H | $OCF_3$ | 6.6–6.9 (Z = $NO_2$), 6.4–6.7 (Z = $NH_2$) |
| 40 | H | $C_3F_7$ | H | $SCH_3$ | |

[a]Benzylic proton quartet, δ(ppm) in CDCl$_3$

What is claimed is:

1. A 2-(alpha-perhaloalkylbenzyloxy)pyridyl compound of the formula

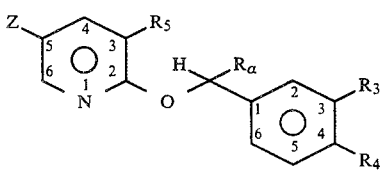

wherein
$R_\alpha$ is a lower perhaloalkyl substituent;
$R_3$ is selected from the group consisting of -hydrogen, -halogen and -phenylthio;
$R_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino; or
$R_3$ and $R_4$ together constitute a —OCH$_2$O—, —CH$_2$C(CH$_3$)$_2$O—, or —CF$_2$CF$_2$O— bridge;
$R_5$ is -hydrogen or -lower alkyl; and
Z is -amino or -nitro.

2. 2-(2,2,2-Trifluoroethoxy-1-phenyl)-3-methyl-5-nitropyridine, a compound of claim 1.

3. 5-Amino-2-(2,2,2-trifluoromethoxy-1-phenyl)-3-methylpyridine, a compound of claim 1.

4. 2-[1-(2,2,3,3-Tetrafluoro-2,3-dihydrobenzofuran-5-yl)-2,2,2-trifluoroethoxy]-5-nitropyridine, a compound of claim 1.

5. 5-Amino-2-[1-(2,2,3,3-tetrafluoro-2,3-dihydrobenzofuran-5-yl)-2,2,2-trifluoroethoxy]pyridine, a compound of claim 1.

6. 2-[1-(1,3-Benzodiox-5-yl)-2,2,2-trifluoroethoxy]-5-nitropyridine, a compound of claim 1.

7. 5-Amino-2-[1-(1,3-benzodiox-5-yl)-2,2,2-trifluoroethoxy]pyridine, a compound of claim 1.

8. 2-[1-(1,3-Benzodiox-5-yl)-2,2,3,3,4,4,4-heptafluorobutoxy]-3-methyl-5-nitropyridine, a compound of claim 1.

9. 5-Amino-2-[1-(1,3-benzodiox-5-yl)-2,2,3,3,-4,4,4-heptafluorobutoxy]-3-methylpyridine, a compound of claim 1.

10. 2-[2,2,3,3,3-Pentafluoro-1-(2,3-dihydro-2,2-dimethylbenzofuran-5-yl)propoxy]-3-methyl-5-nitropyridine, a compound of claim 1.

11. 5-Amino-2-[2,2,3,3,3-pentafluoro-1-(2,3-dihydro-2,2-dimethylbenzofuran-5-yl)propoxy]-3-methylpyridine, a compound of claim 1.

* * * * *